(12) United States Patent
Carrabis

(10) Patent No.: US 8,655,804 B2
(45) Date of Patent: Feb. 18, 2014

(54) SYSTEM AND METHOD FOR DETERMINING A CHARACTERISTIC OF AN INDIVIDUAL

(75) Inventor: Joseph Carrabis, Nashua, NH (US)

(73) Assignee: Next Stage Evolution, LLC, Nashua, NH (US)

(*) Notice: Subject to any disclaimer, the term of this patent is extended or adjusted under 35 U.S.C. 154(b) by 1058 days.

(21) Appl. No.: 12/620,221

(22) Filed: Nov. 17, 2009

(65) Prior Publication Data
US 2010/0076912 A1    Mar. 25, 2010

Related U.S. Application Data

(63) Continuation-in-part of application No. 12/053,064, filed on Mar. 21, 2008, now Pat. No. 7,822,783, which is a continuation of application No. 10/071,731, filed on Feb. 7, 2002, now Pat. No. 7,383,283.

(51) Int. Cl.
*G06F 15/18* (2006.01)
*G01N 33/48* (2006.01)
*G06N 99/00* (2010.01)

(52) U.S. Cl.
CPC ................... *G06N 99/005* (2013.01)
USPC ............................. 706/12; 702/19

(58) Field of Classification Search
USPC ............................................. 706/12
See application file for complete search history.

(56) References Cited

U.S. PATENT DOCUMENTS

| | | | |
|---|---|---|---|
| 3,892,053 A | 7/1975 | Booher | |
| 4,508,510 A | 4/1985 | Clifford | |
| 4,699,153 A | 10/1987 | Shevrin et al. | |
| 4,735,572 A | 4/1988 | Clifford | |
| 4,916,745 A | 4/1990 | Hart et al. | |
| 5,152,290 A * | 10/1992 | Freeland | 600/443 |
| 5,178,149 A * | 1/1993 | Imburgia et al. | 600/463 |
| 5,390,281 A | 2/1995 | Luciw et al. | |

(Continued)

FOREIGN PATENT DOCUMENTS

| | | |
|---|---|---|
| EP | 0855199 A2 | 7/1998 |
| EP | 1083488 A2 | 3/2001 |

OTHER PUBLICATIONS

Sabaz, Mark et al.; "Validation of a New Qualtiy of Life Measure for Children with Epilepsy"; 2000; Lippincott Williams & Wilkins, Inc., Baltimore; Epilepsia, 41(6); pp. 765-774.*

(Continued)

*Primary Examiner* — Jeffrey A Gaffin
*Assistant Examiner* — Stanley K Hill
(74) *Attorney, Agent, or Firm* — Hayes Soloway P.C.

(57) ABSTRACT

A system and method for determining a characteristic of an individual is provided. The method includes determining at least one nonconscious element of an interaction by the individual and correlating the at least one nonconscious element with at least one identifiable demographic characteristic of the individual. The system includes a computerized medium having a human interface system situated to facilitate interaction with the individual and produce a quantity of data corresponding to the interaction. A programmable device is in communication with the computerized medium and is situated to use at least a portion of the quantity of data corresponding to the interaction with the individual to determine at least one nonconscious element of the interaction with the individual. A correlation system is situated to correlate the at least one nonconscious element with at least one identifiable demographic characteristic and output a quantity of resulting information.

14 Claims, 3 Drawing Sheets

(56) References Cited

U.S. PATENT DOCUMENTS

| | | | |
|---|---|---|---|
| 5,682,882 A | 11/1997 | Lieberman | |
| 5,717,825 A | 2/1998 | Lamblin | |
| 5,734,372 A | 3/1998 | Verstockt | |
| 5,987,415 A | 11/1999 | Breese et al. | |
| 6,018,682 A | 1/2000 | Rise | |
| 6,067,565 A | 5/2000 | Horvitz | |
| 6,091,826 A | 7/2000 | Laitinen et al. | |
| 6,157,913 A | 12/2000 | Bernstein | |
| 6,188,777 B1 | 2/2001 | Darrell et al. | |
| 6,230,111 B1 | 5/2001 | Mizokawa | |
| 6,233,545 B1 | 5/2001 | Datig | |
| 6,259,889 B1 | 7/2001 | LaDue | |
| 6,260,034 B1 | 7/2001 | Horvitz et al. | |
| 6,269,275 B1 | 7/2001 | Slade | |
| 6,314,412 B1 | 11/2001 | Yamaguchi et al. | |
| 6,338,051 B1 | 1/2002 | Kang et al. | |
| 6,341,267 B1 | 1/2002 | Taub | |
| 6,346,879 B1 | 2/2002 | Peled | |
| 6,347,261 B1 | 2/2002 | Sakaue et al. | |
| 6,430,523 B1 | 8/2002 | Mizokawa | |
| 6,520,905 B1 | 2/2003 | Surve et al. | |
| 6,604,090 B1 | 8/2003 | Tackett et al. | |
| 6,606,581 B1 | 8/2003 | Nickerson et al. | |
| 6,622,036 B1 * | 9/2003 | Suffin | 600/544 |
| 6,622,140 B1 | 9/2003 | Kantrowitz | |
| 6,629,242 B2 | 9/2003 | Kamiya et al. | |
| 6,655,963 B1 | 12/2003 | Horvitz et al. | |
| 6,714,917 B1 | 3/2004 | Eldering et al. | |
| 6,820,037 B2 | 11/2004 | Simon | |
| 6,874,127 B2 | 3/2005 | Newell et al. | |
| 6,901,390 B2 | 5/2005 | Mizokawa | |
| 6,923,763 B1 * | 8/2005 | Kovatchev et al. | 600/300 |
| 6,928,392 B2 | 8/2005 | Nickerson et al. | |
| 7,058,566 B2 | 6/2006 | Shaw | |
| 7,062,475 B1 | 6/2006 | Szabo et al. | |
| 7,089,218 B1 | 8/2006 | Visel | |
| 7,092,926 B2 | 8/2006 | Cerrato | |
| 7,149,704 B2 | 12/2006 | Martin et al. | |
| 7,162,432 B2 | 1/2007 | Mascarenhas | |
| 7,493,655 B2 | 2/2009 | Brown | |
| 7,496,553 B2 | 2/2009 | Cerrato | |
| 2001/0042004 A1 | 11/2001 | Taub | |
| 2002/0111540 A1 | 8/2002 | Schmidt et al. | |
| 2003/0149975 A1 | 8/2003 | Eldering et al. | |
| 2004/0019518 A1 | 1/2004 | Abraham et al. | |
| 2004/0076936 A1 | 4/2004 | Horvitz et al. | |
| 2004/0234932 A1 | 11/2004 | Hughes et al. | |
| 2005/0053902 A1 | 3/2005 | Vladimirovich | |
| 2005/0192679 A1 | 9/2005 | Strupp | |
| 2006/0173556 A1 | 8/2006 | Rosenberg | |
| 2007/0073681 A1 | 3/2007 | Adar et al. | |
| 2007/0167689 A1 | 7/2007 | Ramadas et al. | |
| 2007/0178428 A1 | 8/2007 | Luchin et al. | |
| 2007/0299631 A1 | 12/2007 | Macbeth et al. | |
| 2008/0059282 A1 | 3/2008 | Vallier et al. | |
| 2008/0081320 A1 | 4/2008 | Hackett | |
| 2008/0140508 A1 | 6/2008 | Anand et al. | |
| 2008/0249968 A1 | 10/2008 | Flinn et al. | |
| 2009/0119154 A1 | 5/2009 | Jung et al. | |
| 2009/0140864 A1 | 6/2009 | Aaron et al. | |

OTHER PUBLICATIONS

Maria Tulberg, "deadweight or turbokick?", paper for presentation at the second national open conference on group and social psychology, Lund May 18-19, 2000.

Simon R. Goerger, "Validating human behavioral models for combat simulations using techniques for the evaluation of human performance", SCSC 2003, pp. 737-747.

U.S. DOT, Evaluation of Techniques for Ocular Measurement as an Index of Fatigue and the Basis for Alertness Management, Apr. 1998.

Neuroeducation Free Information sheets obtained at http://www.neuroeducation.org.uk/pages/epilepsy/whatis.html, entitled "What is Epilepsy?" on Mar. 11, 2005.

Anant Kartik Mithal, "Using psychomotor models of movement in the analysis and design of computer pointing devices", conference companion on Human Factors in computing systems, 1995, pp. 65-66.

Koen Versmissen, "Categorial grammar, modalities, and algebraic semantics", 1992, pp. 337-383.

Jeremy Slocum, "A Breakdown of the psychomotor components of input device usage", Usability New 7.1, 2005, 6 pps.

MoDULE 17: Teaching Psychomotor Skills, National guidelines for educating EMS instructors, Aug. 2002, pp. 139-143.

Jill Coffin, "Leveraging typing phenomena to design one-handed wearable keyboards, proceeding of the 2005 Ninth IEEE International Symposium on wearable computers", 2 pps.

Khan, H., "Procedural steps for designing and implementing an evaluative research using outcome based program evaluation", Frontiers in Education Conference, proceedings, 1995, vol. 1, pp. 2c1.9-2c1.12.

Holly Jimison et al., "Unobtrusive monitoring of computer interactions to detect cognitive status in elders", Information Technology in Biomedicine, IEEE Transactions, vol. 8, Issue 3, 2004, pp. 248-252.

* cited by examiner

SYSTEM AND METHOD FOR DETERMINING A CHARACTERISTIC OF AN INDIVIDUAL

CROSS-REFERENCE TO RELATED APPLICATION

This is a continuation in part application of copending U.S. application entitled, "Programmable method and apparatus for real-time adaptation of presentations to individuals," having Ser. No. 12/053,064, filed Mar. 21, 2008, itself a continuation application of U.S. Pat. No. 7,383,283, the disclosures of which are entirely incorporated herein by reference.

FIELD OF THE DISCLOSURE

The present disclosure is related to determining a characteristic of an individual.

BACKGROUND OF THE DISCLOSURE

Semiotics is a theory of signs and symbols, specifically dealing with their function in both artificially constructed and natural languages, including syntactics, semantics, and pragmatics. Language in all forms is semiotics in action because whenever entities communicate, they do so by exchanging groupings of mutually agreed upon signs. Here, "language in all forms" can be thought of as any interaction between entities (can be the same entity) that results in conscious or nonconscious activity Culture, education, age, ethnicity, etc., all play a role in which signs are mutually agreed upon and how the signs may be used.

Whether people are born with an innate understanding of language is debatable. Barring organic trauma, people are born with an ability to communicate wants, needs, and desires. At some point the innate ability to communicate may be overlaid with an understanding of which specific interactions produce which specific results (an example is "language in all its forms"). This point harkens to one of the rules of semiotic information—"the first communication must be instructions on how to build a receiver."

The construction of language from primitive communication takes the form of the acquisition of psycholexicals, or conceptual primitives. Conceptual primitives are the archetypes of language and often take the form of words that describe things rather than things in themselves. For example, "water" can be thought of as the conceptual primitive of ocean, lake, river, rain, etc. "Big" is closer to being a true conceptual primitive because "big" is used as an adjective in most languages that support such grammar constructs. Conceptual primitives are the building blocks of understanding and recognition of the individual's environment and are the internal precursors of language.

The most basic conceptual primitives are binary and usually comprised of mythic opposites such as "good" and "bad". The child learning to lingualize its experience does so by interacting with its environment in the presence of others with more developed language skills. What usually happens is that the child's first lingualizing experiences of its environment are polarity commands such as "come", "go", "hot", "cold". These lingualizations become conceptual primitives and place the child into a mythic reality due to their polar, binary nature; something either "is" or "is not". Later the child learns that shades of gray exist and begins to experience sensory reality. Language develops when the child begins applying conceptual primitives to create more complex communications. These psycholexicals or conceptual primitives stay with the individual long after sophisticated language skills develop and remain how the individual—regardless of age, gender, or education—initially internalizes information. Further, these psycholexicals are highly culture and language specific.

All language-using species create language semiotically. A child learning to speak learns that certain sounds will be rewarded with certain actions. This is first accomplished by making sounds to be rewarded with objects in the child's immediate surroundings. The child sees a cookie and says, "Cookie", to an American English speaker, the child gets a cookie. If the child were from a different culture and language set, saw a cookie and said, "Bistoli" to a speaker of only American English, the child would be unrewarded. Language is a well-defined set of semiotic equations in which the signifier is culturally accepted as being psycholexically equivalent to the object that is culturally defined.

From this it is derived that any form of communication is a series of semiotic equations. Language is not limited to oral communication. Signed languages such as Ameslan, Singlish, Freslan, etc., contain the same richness of concept spaces, psycholexical primitives, and so on. Further, language generation is not engaged only when the speaker is being heard. An individual that communicates frequently with hand gestures will engage in many of those same hand gestures while on the phone. When a person is engaged with something on the television, that person may speak to the television without any delusion of being heard.

At the point where conceptual primitives become active in communication, they change role from conceptual primitive to modality. A modality is a conceptual primitive, which is active either consciously or unconsciously in the psyche of an individual and comes in two flavors: sensory and internal. Sensory modalities are those conceptual primitives directly related to primate sensory systems (vision, hearing, etc.) as expressed through information exchange and communication. Internal modalities are those conceptual primitives by which information is expressed both to ourselves and to others.

Methods of determining a characteristic of an individual have been used in the past to identify features of the individual or interests of the individual. These methods are sometimes used to identify the individual's interests for marketing purposes, such as targeted marketing practices where a consumer who is likely to purchase a product or use a service is subjected to enhanced marketing. However, these methods involve direct interaction by the individual, such as by prompting the individual to consciously submit information. Generally, information that is consciously submitted is done so through questionnaires, forms, click-boxes on web sites or other types of questioning, such as oral questioning. Gathering information related to a characteristic of an individual in this way is frequently cumbersome, time-consuming and unwanted by the individual being targeted. As a result, the information may be hard to compile and may also be inaccurate, as the individual targeted may fail to provide some information, or provide falsified information.

Thus, a heretofore unaddressed need exists in the industry to address the aforementioned deficiencies and inadequacies.

SUMMARY OF THE DISCLOSURE

Embodiments of the present disclosure provide a system and method of determining a characteristic of an individual. Briefly described, in architecture, one embodiment of the system, among others, can be implemented as follows. The system contains a computerized medium having a human interface system situated to facilitate interaction with the individual and produce a quantity of data corresponding to the interaction. A programmable device is in communication with the computerized medium. The programmable device situated to use at least a portion of the quantity of data corresponding to the interaction with the individual to determine at least one nonconscious element of the interaction with the individual. A correlation system is situated to correlate the at least one nonconscious element with at least one identifiable demographic characteristic and output a quantity of resulting information.

The present disclosure can also be viewed as providing methods of determining a characteristic of an individual. In this regard, one embodiment of such a method, among others, can be broadly summarized by the following steps: determining at least one nonconscious element of an interaction by the individual; and correlating the at least one nonconscious element with at least one identifiable demographic characteristic of the individual.

The present disclosure can also be viewed as providing a computer readable medium to determine a characteristic of an individual. In this regard, one embodiment of a computer readable medium, among others, can be broadly summarized by the following: program code to produce a quantity of data corresponding to an interaction of the individual with a computerized medium; program code to use at least a portion of the quantity of data corresponding to the interaction of the individual to determine at least one nonconscious element of the interaction with the individual; and program code to correlate the at least one nonconscious element with at least one identifiable demographic characteristic and output a quantity of resulting information.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
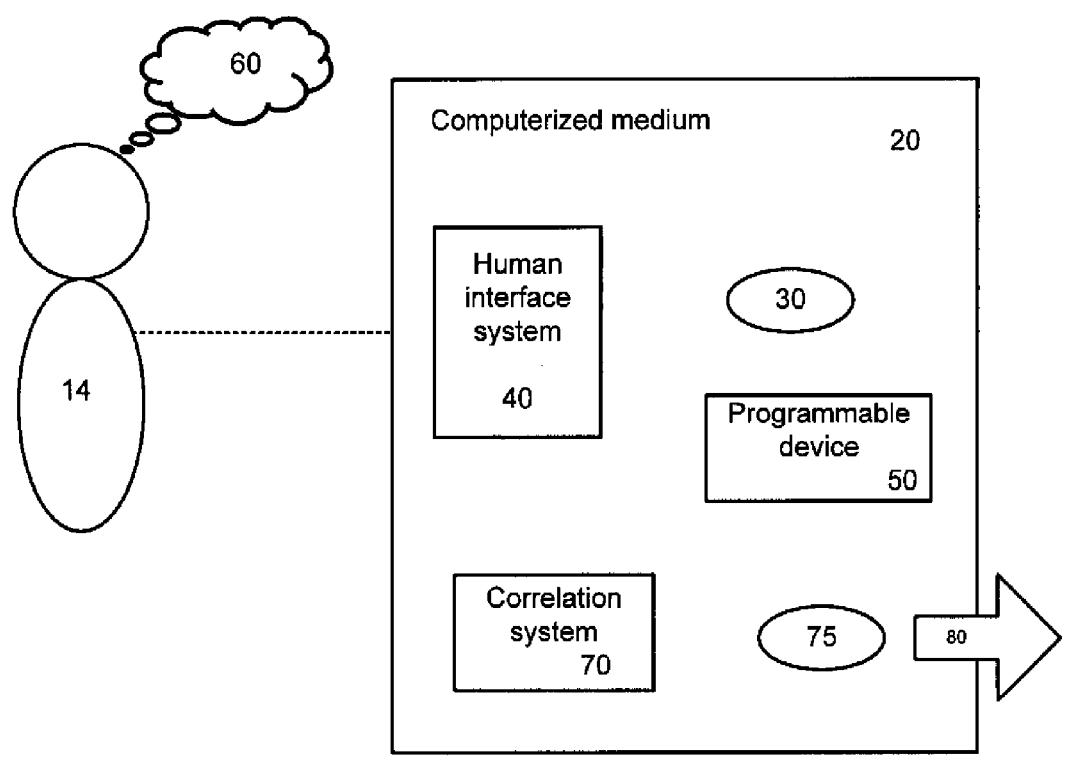
FIG. 1 illustrates a block diagram of a system for determining a characteristic of an individual, in accordance with a first exemplary embodiment of the present disclosure.

The present disclosure uses psychometrics, a concept related to biometrics except that the technology relates to a person's thought patterns as opposed to biological traits. The difference allows psychometrics to generate value in applications presently addressed by biometrics as well as applications for which biometrics is too limited. Therefore the detailed description of the claimed disclosure is briefly prefaced with an enabling description of psychometrics as it relates to one of many applications.

Psychometrics relies on principles from psychomotor research. One application of the present disclosure combines psychometrics and the latest in web technologies to link what happens in the viewer's mind to what happens to the mouse and keyboard to what happens to the machine interface focal point (e.g., a cursor) to what happens on the screen. The following definitions establish the context with which to understand the present disclosure:

1) The person sitting at their computer, browsing a website, is the viewer;

2) The viewer is looking at web sites or other electronic interfaces via a browser;

3) The viewer's browser is at least partially controlling what is displayed (parts of web pages, new web pages, etc) on the computer monitor by hand motion on a pointing device called a mouse and by keystrokes on the keyboard;

4) The mouse has a symbolic representation on what is displayed via the machine interface focal point (e.g., a cursor);

5) The viewer navigates the browser by using the mouse to move the machine interface focal point and then clicking on an action item on the currently presented page;

6) Whatever is currently shown in the browser window may be viewed as a single presentation from the web site. This current browser window may consist of frames and other complexities but still represents a single presentation to the viewer. A presentation may include other output, such as audio transmissions, for the viewer; and 7) The machine interface focal point and presentation are the interface between the viewer and the web server which is delivering content to the browser for display.

People, regardless of cultural origin or life experience, have a psychometric tendency known as "egocentric localization." An individual's egocentric localization is their sense of where their body is positioned relative to other objects in the external environment. Thus, our viewer knows intuitively that they are sitting at their computer, knows where the computer is in relation to where they are sitting, knows where the keyboard is having only glanced at it once, knows where the mouse is having only glanced at it once, etc.

Individuals also have the ability to perceive the distances between objects within their environment. This ability is known as "object-relative localization." Object-relative localization means not only does the viewer know that they're sitting, that they are looking at their monitor to see their browser, that their hands are at or near the keyboard, and that one hand may be on the mouse from time to time, but it also means that the viewer intuitively knows the distances and spatial relationships between the monitor, the keyboard, the mouse, their seat, the top of their desk, etc.

It is important to remember that all this is being done nonconsciously.

As you read this, you are engaged in a flurry of activity of which most people are totally unaware. You are demonstrating a cognitive psychomotor process called "selective attention in vision." This means you're reading parts of this text, basically breaking the entire document into separate elements which are more easily visually digested and processed. The reason you are demonstrating selective attention in vision is because when you read, when you look at a picture, when you look at anything that requires the processing of non-remembered information, you are performing a "visual search task" and the search is for "pictoral or monocular cues" which cause your eye to tell your brain that the information your mind is seeking has been found. These concepts have a vast history in neuroscience and cognition studies.

Studies indicate that everyone projects their internal reality onto their external world. This is known as "mapping." As you read this, chances are you're making evaluations of what is written—deciding if you agree or disagree. In either case, you're taking your internal reality (the decision to agree or disagree and the thoughts that led to that decision) and projecting it onto your external world (these words as they appear in your browser or on a printed page). You're applying a part of your internal reality—what makes sense, what's valid, what you're willing to accept as true—and using it as a test for some stimulus in your external world—the information being offered herein.

When you take action based on some projection of your internal reality onto your external world, you've demonstrated a "cognitive-motor map." The "map" part we explained above. The "motor" part comes from the action taken. The "cognitive" part comes from the decision you made after doing some information processing. All of these parts deal with "eye movement and information processing." Eye movement and information processing are closely related because one cannot happen without the other. Even someone staring off into space thinking is nonconsciously performing minute contractions of the eye muscles as thoughts slide into and out of place.

Because human beings are wired the way they are, your body tracks where your eyes are looking. Unless we're being coy or trying to see something with peripheral vision, we tend to "face things head on." This is especially true when we're searching for something (as in "visual search task"). We "face tasks head on" because it allows us to bring the full implementation of our cognitive-motor maps to bear on the problem; both eyes are focusing on the target, the ears are equidistant and our auditory system is focused, even our hands tend to go into acquisitional behavior (you're ready to reach for something). When using the computer our hands normally do not come off the keyboard or the mouse until we are done processing and begin evaluating (mapping). Then, at some point, our hands go back to where they were . . . almost. For example, moving your hands from mouse to keyboard or vice-versa. This action indicates that some nonconscious decision was made to operate differently in the environment.

Because people all over the world are physiologically wired substantially similarly, people all over the world have "sensory motor learning" experiences. As a child learns to catch a ball, they get bopped by the ball a few times before they learn to coordinate what their eye sees with what their hands do. Sensory motor learning is necessary because normal perceptual development depends upon active bodily movement under higher sensory (visual, auditory, kinesthetic) guidance. But there are two aspects to sensory motor learning. The aspect of motor learning that occurs watching TV or going to the theater is called "exafference." Exafference is stimulation that acts upon a passive observer. The second aspect of motor learning involves more "audience involvement" and is called "reafference." Reafference is stimulation that changes as a result of an individual's own movements—like moving your mouse or using your keyboard to alter the interface that appears in your browser.

Finally, the "stimulus control and attention" concept tells us that an individual's attention tends to focus where that individual is able to control the amount of stimulus given. When you work on a car, you want a good light to see what you are doing. You focus the light in the area of the car you are working to see better. And, of course, the light allowed you to focus your attention on a certain part of the car, bringing it into better visual focus than the other parts in the car.

A viewer is sitting at a computer, using a browser to perform a visual search task and something in the presentation provides a pictorial or monocular cue that causes the viewer's brain to suspend eye movement. The suspended eye movement signals the viewer's mind to alter the information processing it is doing, briefly. Whatever this pictorial or monocular cue was, the viewer's brain needs to control the amount of stimulus in order to focus the viewer's attention. These actions are where sensory motor learning and reafference come in to play. The viewer will focus attention by using the mouse or keyboard to move the machine interface focal point or enter some data (a command, text, etc.) to whatever caught the viewer's attention. These actions may, and likely all, happen nonconsciously.

Even if the viewer's hands were tied so that they could only come free when the viewer was ready to request the next presentation, the sensory motor system knows where your attention was and will not rest until it has done its job. Its job is to make some part of the viewer's body make some kind of movement in the cue's direction (even when there are multiple cues being processed). The movement may be minute, but it will happen unless the viewer has tremendous physical training and control to resist the movement. The viewer's eyes go where the mind was and the hands are sure to follow. In the case of a web browser, the cursor (or any machine interface focal point), an extension of the hands, will follow.

Psycho-, socio-, and neuro-linguistics teach that at the highest level, everybody has the same maps because everybody has the same set of sensory apparatus. These same three disciplines teach that as you go deeper and deeper, everybody's maps change to the point where you can tell from a single sentence much about an individual's life and state of mind.

As described herein, people project their internal reality externally. This projection helps us know who we are, our boundaries, our limits, our friends and our neighbors. When a viewer is sitting at a browser, the viewer projects their internal reality onto the presentation in the browser window.

When the viewer projects their internal reality onto the presentation, they are looking for something to connect to, something which is familiar at some level and to which they can use as a reference for everything else on the screen. Individuals do this in the real world via the sense of egocentric localization. Individuals do this in the virtual world by using the cursor (machine interface focal point) and the brain's abilities to recognize patterns and discriminate familiar patterns from less familiar ones. In a very real sense, the cursor takes the place of our hand. Thus, an individual's "virtual" egocentric location is referenced by the cursor's position on the screen.

Just as virtual egocentric localization occurs when an individual finds out where the cursor is within the presentation, object-relative localization occurs when the individual determines where everything else is on the screen in relation to the cursor (hence the term 'machine interface focal point'). Once the viewer finds out where everything is on the screen via a quick glance, they start parsing. It doesn't matter if they are reading text or looking at pictures, the viewer will parse the presentation into easily processable pieces of information. This especially occurs if the viewer wants to remember the information.

To be clear, people don't "read" web pages as they "read" a book. Usually they scan and, when scanning, they tend to use a stimulus control to focus their attention on what they are reading because there's so much visual noise on the page they can't focus otherwise. Stimulus control is the individual in the guise of the machine interface focal point. On the computer, we control stimulus via the mouse and keyboard. Specifically, parsing the presentation requires an individual's body to match their selective attention in vision to selective movement in the body due to sensory-motor learning and reafference. In other words, where the eyes go, the cursor (machine interface focal point) will follow. The association of eyes and cursor can be accomplished by using a mouse to move the cursor to where the eyes are going, by scrolling a page to bring the location where the eyes are going to the cursor, or otherwise utilizing one or more input devices to bring the cursor and object of the eyes into at least partial alignment.

Humans have as many modalities as they have senses (which exceed the five primary senses taught). For example, if a viewer is sitting at their browser looking at a presentation and a pictorial or monocular cue occurs, if their hand is on the mouse or keyboard, the cursor (machine interface focal point) will move minutely if not grossly (in the sense of motor movement) towards that cue. There is a definite distance associated with the movement of the cursor from where it started to where it ended up. Before the viewer clicks on anything, the viewer is merely attempting to focus their attention by controlling the stimulus. Because the presentation (as presented on a computer monitor) is basically a two dimensional grid, the path the cursor takes, which is governed by the viewer's mouse movement, can be measured as:

$$f(\text{distance})=Dx+Dy$$

There is more than just linear distance associated with moving the cursor (machine interface focal point). Forcing the viewer to visually search for pictorial or monocular cues on a presentation is highly desirable because doing so takes time. When we add time to the simple equation above we get something more like this:

$$f(\text{movement})=(Dx/Dt)+(Dy/Dt)$$

Also, a path is not a simple (X1-X0)+(Y1-Y0) distance. A path, like a path in the woods, means avoiding things, going around others, taking the best route possible when the egocentric localizing viewer determines what is around in the object-relative localizing way. Even though the actual mouse motions may have been minute, the viewer was parsing that interface to focus attention. Therefore, the equation more resembles:

$$f(\text{sensory motor activity})=*t((dx/dt)+(dy/dt))$$

But the sensory-motor activity is tied to the cognitive-motor map because the brain (cognitive) is telling the body (motor) what to do based on what the eyes are telling it (sensory). Specifically, the brain is doing lots of work to direct attention to what the mind wants to know and it's doing it along sensory modality channels, so the equation is really:

$$\int_x\int_y\int_t(\text{attention})\partial x\partial y\partial t = \int_x\int_y\int_t(*(\text{sensory modality})f(\text{modality})(\partial x/\partial t)+*(\text{sensory modality})f(\text{modality})(\partial y/\partial t)+*(\text{sensory modality})f(\text{modality})(\partial t/\partial x))\partial x\partial y\partial t$$

The best part about this equation is that the *(sensory modality) f(modality) parts—which relate to the visual, auditory and kinesthetic sensory modalities—of the above equation are fairly well known and have been documented for about the past 25 years. Also, these equations are the reduced form of the general technology equation $$f(\text{attention})=_{j=1}\Gamma^\infty(\Sigma_i f(\text{modality}_i)(\delta j/\delta t)\cdot_{j=1}\Gamma^n(\delta j/\delta t)(d^n i/dt^n))$$

||j=dimension counter, i=modality counter, which accounts for a plurality of environments and a plurality of degrees of freedom within that environment.

The science surrounding psychomotor behaviors has been developing for some time. However, the application of the science to determining a characteristic of an individual is new. As individuals continue to become more accustomed to using digital devices, and activities hosted on digital devices, the concept of tracking an individual's nonconscious behaviors using the digital devices becomes increasingly convenient.

Programmable code within a software program can track cursor (machine interface focal point) movement through time (meaning velocity and acceleration, relative position and distancing). The software program may send a string of variables back to the web server. This string of variables can contain a string of (X,Y,T) triplets decoded by server-side software to determine movement through a grid and time in each quadrant (the quadrant sizes can be manipulated as dictated by presentation needs). When grid movement is determined, the modality summations can be selected to determine if the viewer's attention is focused on visual, auditory, kinesthetic or other related cues.

Based on the results of this equation, the web server can prepare in real time what the next presentation and interface should be in order to capture more of the viewer's attention by presenting the web content in modalities which the viewer has nonconsciously selected. Thus, content is directed via a smart web server to a viewer based on the viewer's nonconscious selection.

Returning to a previously discussed equation: f(movement)=(Dx/Dt)+(Dy/Dt), movement is the measure of cursor movement over the presentation. From any starting point on a presentation, the cursor movement is a series of ordered doublets, ((X,T), (Y,T)), where X and Y represent distance along a Cartesian grid, for example, and T is the time of each movement. There are several software packages and software languages that monitor cursor movement over a presentation for the purposes of pop-ups and the like, and there are several input devices for moving the cursor other than with the mouse. All of these methods are commonly available over the Internet and the input devices and associated operation language do not constitute a unique part of this disclosure.

Each presentation sent by the present system carries a set of specific meta-tags. One of these meta-tags acts as a session-id. Each presentation itself is mapped to an interface grid, which is useful for the scripting language of the disclosure. The interface grid may have a series of reference targets that allow the system to know where the original cursor position was on each presentation by determining Dx and Dy via cursor movement before crossing any reference target. It has been demonstrated that the complexity of any presentation system can be determined by the equation: $1/a+1/.beta.+1/.gamma.=1$ where a, .beta. and .gamma. represent the complexity of the presentation format, the web server and the data server respectively. Each of these variables can be tiered so that the above equation can represent a very large web system. It was also demonstrated that it is possible to atomize any presentation so that the most minute changes in the presentation can be managed by a sufficiently designed server system. The user of web server, data server, etc., are for the simplified discussion of a web system. The system and the equations given may be part of an Information Driven Presentation Architecture.

When a known viewer requests a presentation through the system of the present disclosure, they are sent an instantiation, which may be a unique presentation. The web server system also sends the instantiation to the engine. The instantiation also contains the viewer identification. As the viewer moves about the presentation, their interface collects ((x,t), (y,t)) doublets and sends them back to the engine at some interval which is determined from the above equation. The engine uses these doublets and the present instantiation as data for the equations, which allows the engine to determine a viewer's modalities and attention.

The present disclosure is directed to determining a characteristic of an individual. FIG. 1 illustrates a block diagram of a system 10 for determining a characteristic of an individual 14, in accordance with a first exemplary embodiment of the present disclosure. The system 10 includes a computerized medium 20 having a human interface system 40. The human interface system 40, which is situated to facilitate interaction with the individual 14 and produce a quantity of data 30 corresponding to the interaction. A programmable device 50 is in communication with the computerized medium 20. The programmable device 50 is situated to use at least a portion of the quantity of data 30 corresponding to the interaction with the individual 14 to determine at least one nonconscious element 60 of the interaction with the individual 14. A correlation system 70 is situated to correlate the at least one nonconscious element 60 with the at least one identifiable demographic characteristic 75 and output a quantity of resulting information 80.

The computerized medium 20 may include any computerized system, terminal, network or database. Generally, the computerized medium will be the personal computer of the individual 14. However, the computerized medium 20 may also include any other computerized system, such as a server hosting a website or a network of computers in communication. The computerized medium 20 may also include other computerized devices such as a cell phone, an MP3 player, a personal digital assistant, a computer system within an automobile, train or plane, a television, a home security system, or any other computerized medium known to those having ordinary skill in the art.

The computerized medium 20 has at least one human interface system 40, which is situation to facilitate an interaction with the individual 14. The interaction may include an influence or any number or type of activities. If more than one interaction is present, it may be independent or dependent on another interaction. The interaction may be characterized as an action or influence that is capable of being sensed or detected by an object or entity.

The computerized medium 20 may produce a quantity of data 30 corresponding to the interaction. The quantity of data 30 may be produced in any form, including, but not limited to computerized data, textual data and electronic data. A variety of other types of quantity of data 30 may also be produced, as would be recognized by one having ordinary skill in the art. Generally, the interaction is one that is capable of being transposed in the computerized medium 20, or the interaction is an influence of or on the individual 14 that can be sensed or detected by the computerized medium 20. Common examples of the interaction may include moving a mouse such that a cursor (machine interface focal point) is moved on a display screen. Likewise, engaging a key on a keyboard or engaging a touch screen display device may also be an interaction that can be used to produce the quantity of data 30. Other types of interactions may be detected in other ways, such as by monitoring the eye movement of an individual 14 or by monitoring another physical trait of the individual 14.

The interaction with the individual 14 may occur through physical contact or without physical contact. In either case, a human interface system 40 may be the primary component of the computerized medium 20 to facilitate the interaction, and is situated to facilitate interaction between the individual 14 and the computerized medium 20. Accordingly, the human interface system 40 may include a mouse, a keyboard, an eye-monitoring system, a touch screen and/or a microphone. The human interface system 40 may also include any other systems to facilitate interaction, which may include facilitating interaction with a conscious element in addition to the nonconscious element 30. The human interface system 40 may also include a human interface output, such as a display screen notification, an audible notification, a written notification, or any other notifying action, such as allowing entry into a secured area. Any human interface output included within the system 10 is considered within the scope of the present disclosure, however, a human interface output is not required. The human interface system 40 may also include other systems to facilitate interaction with the individual 14, and may include any components or combinations of components that are known to those skilled in the art to be used in facilitating a human interaction with a computerized medium 20.

A programmable device 50 is in communication with the computerized medium 20. As illustrated in FIG. 1, all components within the computerized medium 20 may be in communication with each other. Therefore, the programmable device 50 may be in communication with any components of the computerized medium 20, such as the human interface system 40. The programmable device 50 is situated to use at least a portion of the quantity of data 30 corresponding to the interaction with the individual 14 to determine at least one nonconscious element 60 of the interaction with the individual 14. The communication between the programmable device 50 and any other component may be created by any known connection, including a wireless connection, a hardwired connection, a network connection or an integral connection. The programmable device 50 may also be hosted or incorporated within any other component of the system.

In FIG. 1, the programmable device 50 is illustrated as being hosted in the computerized medium 20. However, the programmable device 50 may commonly be hosted in or integral with the human interface system 40, or it may be external to both the computerized medium 20 and the human interface system 40. The programmable device 50 is situated to determine at least one nonconscious element 60, which may be any mental functioning of the individual 14 that is not represented in consciousness. Commonly, the at least one nonconscious element 60 of the individual is a psychomotor behavioral element of the individual 14.

The correlation system 70 is situated to correlate the at least one nonconscious element 60 with at least one identifiable demographic characteristic 75 and output a quantity of resulting information 80. The correlation system 70 may include a variety of systems capable of correlating data, such as a computerized system having programmable code or a non-computerized electronic correlation system. Correlating the nonconscious element 60 with the at least one identifiable demographic characteristic 75 of the individual 14 may be used to produce at least a portion of the quantity of resulting information 80. Additionally, the correlation system 70 may also include a variety of other actions beyond producing resulting information 80, such as performing a comparison of data, analyzing data, retrieving information from a database, executing instructions identified by a programmable code and storing data or information.

The identifiable demographic characteristic 75 can be any distinguishing trait, quality or property that the individual 14 has. Commonly, the identifiable demographic characteristic 75 will be the individual's 14 age or gender, or a combination thereof. The identifiable demographic characteristic 75 may be one that is determined within a certain parameter of precision, or it may be given within a broad parameter. For example, if the identifiable demographic characteristic 75 of the individual 14 is age, then the age may be given in terms of an upper and/or lower limit, such as older than 50 years old or younger than 30 years old. Additionally, the age may be given in a range, such as where the individual 14 is determined to be between the ages of 25 and 30, or the age plus or minus a number of years, such as 27+/−2 years, or the age may be given by descriptive terms, such as "young" or "old." All ranges and limits may be given and are considered within the scope of the present disclosure. Likewise, if the identifiable demographic characteristic 75 is gender, the output will include information indicative of whether the individual 14 is a male or female.

The system 10 may also include other features and functions. The system 10 may be able to output information associated with an identifiable demographic characteristic 75 that indicates a degree of precision or accuracy of the identifiable demographic characteristic 75. For example, the system 10 may output an identifiable demographic characteristic 75 that the individual is a male or female within 90% confidence. Additionally, the system 10 may include other communication connections to facilitate the transfer of information from or to the system 10. While each component of the system 10 is illustrated as only one object, any of the computerized medium 20, the human interface system 40, the programmable device 50 and the correlation system 70 may be formed by multiple devices operating cooperatively (e.g., the computerized medium 20 may be a combination of a processor, a server, computer code and a display device).

Figure 2:
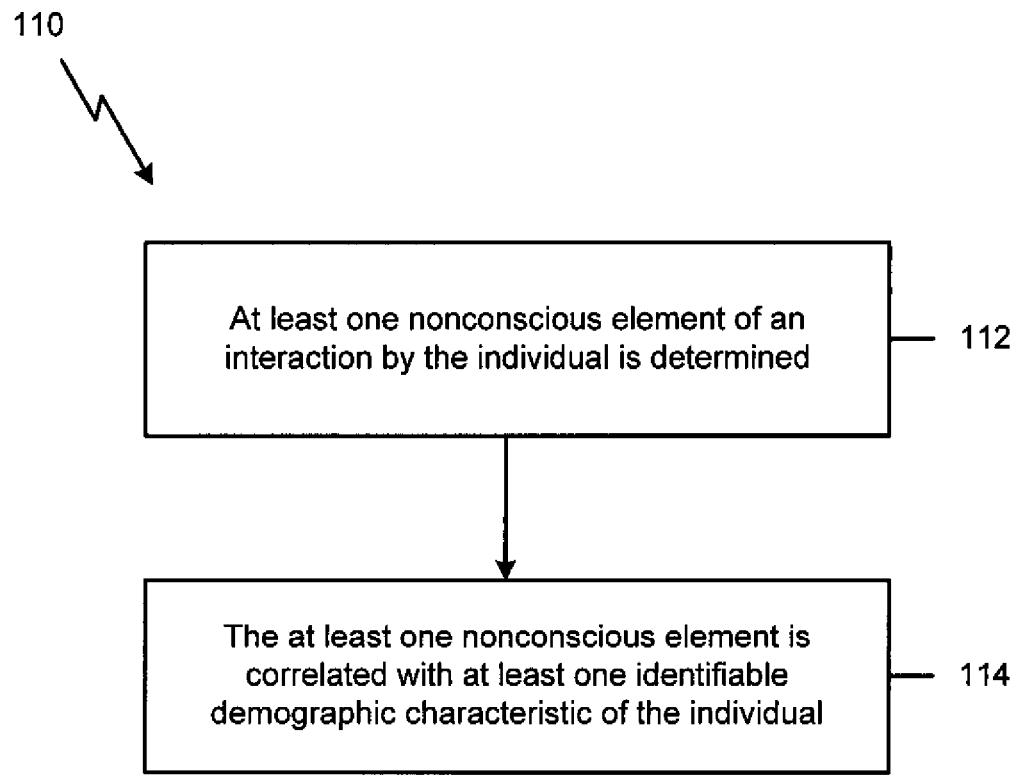
FIG. 2 is an illustration of a method of determining a characteristic of an individual, in accordance with a second exemplary embodiment of the present disclosure.

FIG. 2 is an illustration of a flowchart 110 of a method of determining a characteristic of an individual, in accordance with a second exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

The method of determining a characteristic of an individual may include at least one nonconscious element of an interaction by the individual is determined (block 112). The at least one nonconscious element is correlated with at least one identifiable demographic characteristic of the individual (block 114). The nonconscious element may be any mental functioning of the individual that is not represented in consciousness. Commonly, the nonconscious element of the interaction may be a psychomotor behavioral element of the individual. The nonconscious element may be determined through a determination device, which may include a computerized device, such as a computer having programmable code, or a non-computerized device.

The step of correlating the at least one nonconscious element with at least one identifiable demographic characteristic of the individual may include a variety of systems capable of correlating data, such as a computerized system having programmable code or a non-computerized electronic correlation system. Correlating the nonconscious element with an identifiable demographic characteristic may include a resulting quantity of information, which may be output. However, a variety of other actions, such as performing a comparison of data, analyzing data, retrieving information from a database, executing instructions identified by a programmable code and storing data or information.

The identifiable demographic characteristic may be any distinguishing trait, quality or property that the individual has. Commonly, the identifiable demographic characteristic will be the individual's age or gender, or a combination thereof. The identifiable demographic characteristic may be one that is determined within a certain parameter of precision, or it may be giving within a broad parameter. For example, if the identifiable demographic characteristic of the individual is age, then the age may be given in terms of an upper and/or lower limit, such as older than 50 years old or younger than 30 years old. Additionally, the age may be given in a range, such as where the individual is determined to be between the ages of 25 and 30, or the age plus or minus a number of years, such as 27+/−2 years, or the age may be given by descriptive terms, such as "young" or "old". All ranges and limits may be given and are considered within the scope of the present disclosure. Likewise, if the identifiable demographic characteristic is gender, the output will include information indicative of whether the individual is a male or female.

The nonconscious element may include a psychomotor behavioral element, and the method 110 may include the step of determining at least one modality of the individual based on the psychomotor behavioral element of the interaction. The step of determining a preferred combination of modalities from the at least one modality and ordering the preferred combination of modalities by preference may also be included. This may further define a focus of the individual's attention. An order of the preferred combination of modalities may be calculated by the equation: $\Sigma \int_{-\infty}^{\infty} ((\Sigma G_i(\delta x_i/\delta_i t))/(\Sigma G_i (dx_i/dt_i))) dG_i dt_i \propto \Psi(G)$. The method 110 may also include an additional number of steps. For example, the step of defining a psychodynamic behavioral model and a cognitive behavioral model using the preferred combination of the modalities and the ordering of the modalities may be included.

Additionally, steps relating to the production of a report may also be provided in the method 110. These steps may include repeating the method for a plurality of individuals; aggregating at least one identifiable demographic characteristic for each of the plurality of individuals determined; and producing a report containing at least one identifiable demographic characteristic for each of the plurality of individuals. The report may be something as simple as a graph or figure that conveys some information from a quantity of aggregated data. If, for instance, a web page is viewed by one thousand people and four hundred of them experience confusion at the same passage, the aggregated data may indicate to the web page publisher that there is a confusing passage that needs to be clarified. Similarly, aggregated data may show demographic information of the individuals visiting the site, such as age or gender, based on the sensed nonconscious element of the individuals.

The method 110 may also include the step of storing the determined at least one nonconscious element of the activity in a database. The nonconscious element may be stored in terms of preferred representational geometries via linear algebraic transforms, or by any other storing process. The database may correspond to an identifiable demographic characteristic of the individual.

Figure 3:
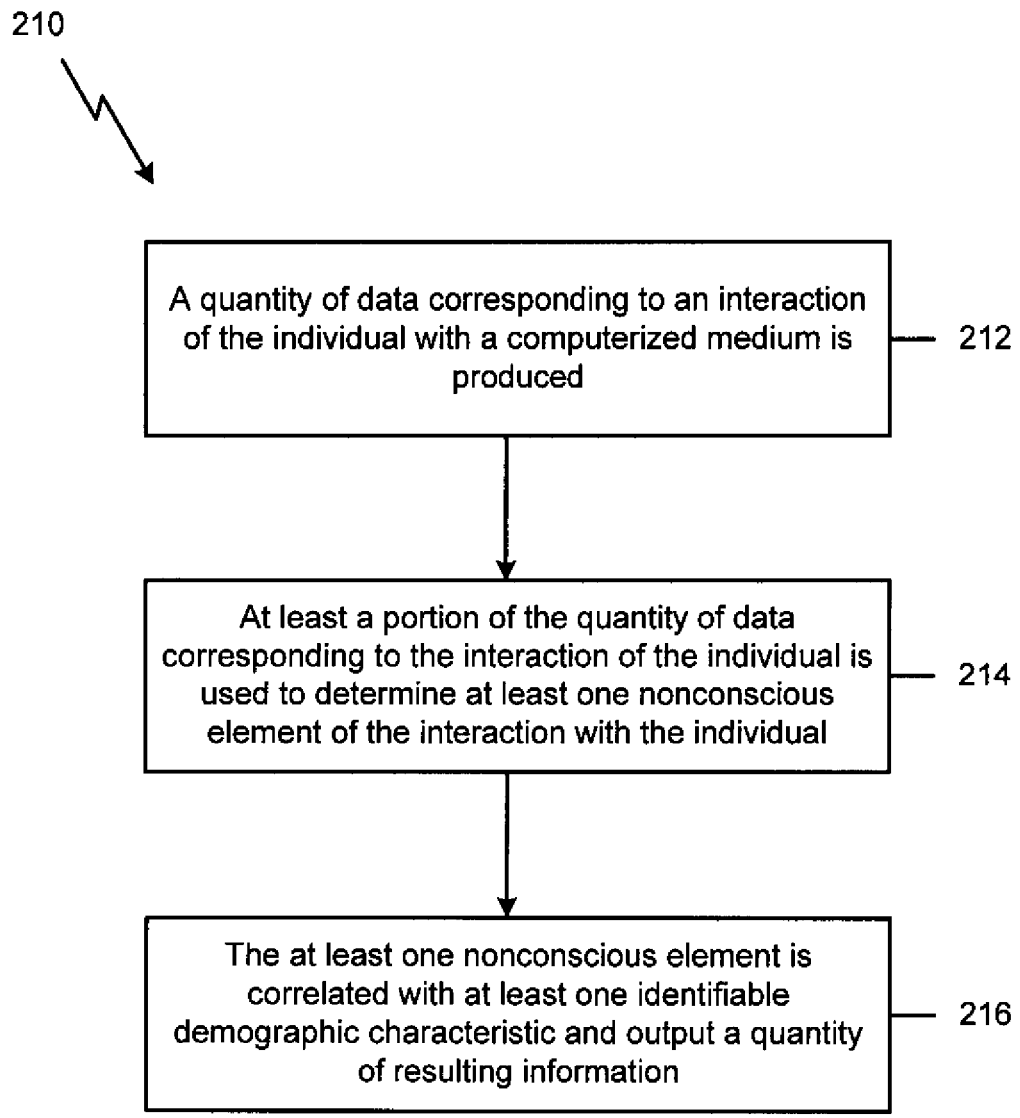
FIG. 3 is an illustration of instructions for a computer readable medium encoded with computer readable program code to determine a characteristic of an individual, in accordance with a third exemplary embodiment of the present disclosure

FIG. 3 is an illustration of a flowchart 210 of a program code within a computer readable medium to determine a characteristic of an individual, in accordance with a third exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As illustrated by the flowchart 210, a quantity of data corresponding to an interaction of the individual with a computerized medium is produced (block 212). At least a portion of the quantity of data corresponding to the interaction of the individual is used to determine at least one nonconscious element of the interaction with the individual (block 214). The at least one nonconscious element is correlated with at least one identifiable demographic characteristic and output a quantity of resulting information (block 216).

The nonconscious element of the interaction of the individual may include a psychomotor behavioral element. The identifiable demographic characteristic of the individual may be at least one of age and gender. Additionally, the program code may determine at least one modality of the individual based a psychomotor behavioral element. The program code may determine a preferred combination of modalities from the at least one modality and an ordering of the preferred combination of modalities by preference thereby further defining a focus of the individual's attention. The preferred combination of modalities may be calculated by an equation: $\Sigma\int_{-\infty}^{\infty}((\Sigma G_i(\delta x_i/\delta_i t))/(\Sigma G_i(dx_i/dt_i)))dG_i dt_i \propto \Psi(G)$.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

What is claimed is:

1. A method of determining a characteristic of an individual, the method comprising:
   electronically recording an interaction of an individual;
   determining at least one nonconscious element of the interaction by the individual; and
   calculating at least one identifiable demographic characteristic of the individual based at least in part on the at least one nonconscious element using a programmable device, wherein the at least one identifiable demographic characteristic of the individual is at least one of age and gender.

2. The method of claim 1, wherein the nonconscious element further comprises a psychomotor behavioral element.

3. The method of claim 1, further comprising the step of determining at least one preferred modality of the individual based on the nonconscious element of the interaction.

4. The method of claim 3, further comprising the step of determining a preferred combination of modalities from the at least one preferred modality and ordering the preferred combination of modalities by preference thereby further defining a focus of the individual's attention.

5. The method of claim 4, further comprising the steps of defining a psychodynamic behavioral model and a cognitive behavioral model using the preferred combination of the modalities and the ordering of the modalities.

6. The method of claim 1, further comprising the steps of:
   repeating the method for a plurality of individuals;
   aggregating at least one identifiable demographic characteristic for each of the plurality of individuals determined; and
   producing a report containing at least one identifiable demographic characteristic for each of the plurality of individuals.

7. The method of claim 1, further comprising the step of storing the determined at least one nonconscious element of the activity in a database, wherein the determined at least one nonconscious element is stored in terms of preferred representational geometries via linear algebraic transforms.

8. The method of claim 7, wherein the database corresponds to an identifiable demographic characteristic of the individual.

9. A system for determining a characteristic of an individual comprising:
   a computerized medium having a human interface system situated to facilitate interaction with the individual and produce a quantity of data corresponding to the interaction;
   a programmable device in communication with the computerized medium, the programmable device situated to use at least a portion of the quantity of data corresponding to the interaction with the individual to determine at least one nonconscious element of the interaction with the individual; and
   a correlation system, situated to calculate at least one identifiable demographic characteristic based at least in part on the at least one nonconscious element and output a quantity of resulting information, wherein the at least one identifiable demographic characteristic of the individual is at least one of age and gender.

10. The system for determining a characteristic of an individual of claim 9, wherein the at least one nonconscious element of the interaction with the individual is a psychomotor behavioral element of the interaction.

11. A non-transitory computer readable medium to determine a characteristic of an individual, the non-transitory computer readable medium comprising:
    program code to produce a quantity of data corresponding to an interaction of the individual with a computerized medium;
    program code to use at least a portion of the quantity of data corresponding to the interaction of the individual to determine at least one nonconscious element of the interaction with the individual; and
    program code to calculate the at least one nonconscious element with at least one identifiable demographic characteristic and output a quantity of resulting information, wherein the at least one identifiable demographic characteristic of the individual is at least one of age and gender.

12. The non-transitory computer readable medium of claim 11, wherein the nonconscious element of the interaction with the individual further comprises a psychomotor behavioral element.

13. The non-transitory computer readable medium of claim 12, further comprising program code to determine at least one modality of the individual based on the psychomotor behavioral element.

14. The non-transitory computer readable medium of claim 13, further comprising program code to determine a preferred combination of modalities from the at least one modality and an ordering of the preferred combination of modalities by preference thereby further defining a focus of the individual's attention.

* * * * *